(12) United States Patent
Binner et al.

(10) Patent No.: US 6,450,986 B1
(45) Date of Patent: Sep. 17, 2002

(54) TAMPON APPLICATOR HAVING OUTWARDLY FLARED RIM (75) Inventors: Curt Binner, Somerset, NJ (US); Gary Vogt, Newtown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/596,469

(22) Filed: Jun. 19, 2000

(51) Int. Cl.[7] .................................................. A61F 13/20
(52) U.S. Cl. ....................................................... 604/15
(58) Field of Search ........................ 604/11–18, 57–60, 604/285–288

(56) References Cited

U.S. PATENT DOCUMENTS

| | | | |
|---|---|---|---|
| 1,191,736 A | * | 7/1916 | Roberson |
| 2,330,257 A | | 9/1943 | Bailey |
| 2,476,956 A | * | 7/1949 | Bonham |
| 2,739,593 A | * | 3/1956 | McLaughlin |
| 2,854,978 A | | 10/1958 | Millman et al. |
| 2,934,068 A | * | 4/1960 | Graham, Jr. et al. |
| 2,998,010 A | | 8/1961 | Griswold et al. |
| 3,005,456 A | | 10/1961 | Graham, Jr. |
| 3,055,369 A | | 9/1962 | Graham, Jr. |
| 3,068,867 A | | 12/1962 | Bletzinger et al. |
| 3,139,886 A | * | 7/1964 | Tallman et al. |
| 3,177,872 A | * | 4/1965 | Pearman |
| 3,320,956 A | | 5/1967 | Steiger |
| 3,559,646 A | | 2/1971 | Mullan |
| 3,618,607 A | | 11/1971 | Ells et al. |
| 3,706,311 A | | 12/1972 | Kokx et al. |
| 3,731,686 A | | 5/1973 | Chatterjee |
| 3,834,389 A | | 9/1974 | Dulle |
| 4,104,013 A | | 8/1978 | Kelly et al. |
| 4,278,088 A | | 7/1981 | Reeves et al. |
| 4,286,595 A | | 9/1981 | Ring |
| 4,291,696 A | | 9/1981 | Ring |
| 4,312,348 A | | 1/1982 | Friese |
| 4,412,833 A | | 11/1983 | Wiegner et al. |
| 4,498,899 A | * | 2/1985 | Gross |
| 4,508,531 A | | 4/1985 | Whitehead et al. |

(List continued on next page.)

FOREIGN PATENT DOCUMENTS

| | | |
|---|---|---|
| FR | 583288 | 10/1924 |
| WO | WO 96/23476 | 8/1996 |
| WO | PCT/US01/19027 | 6/2001 |

OTHER PUBLICATIONS

U.S. patent application Ser. No. 08/594,485, (J&J 1580).
U.S. patent application Ser. No. 09/375,722, (J&J 1834).
U.S. patent application Ser. No. 09/454,989, (J&J 1733).

Primary Examiner—Dennis Ruhl (57) ABSTRACT

An applicator device for inserting an object into a mammalian body cavity includes a tubular member having a rim disposed at one end thereof. The rim has a shoulder projecting outwardly from the tubular member and a return margin directed inwardly from the shoulder distal the tubular member. The invention is especially useful in manufacturing paperboard applicators, such as tampon applicators.

31 Claims, 6 Drawing Sheets

U.S. PATENT DOCUMENTS

| | | |
|---|---|---|
| 4,543,086 A | 9/1985 | Johnson |
| 4,573,964 A | 3/1986 | Huffman |
| 4,699,610 A | 10/1987 | Hanano et al. |
| 4,726,805 A * | 2/1988 | Sanders, III |
| 4,755,164 A | 7/1988 | Hinzmann |
| 4,822,332 A | 4/1989 | Kajander |
| 4,846,802 A * | 7/1989 | Sanders, III |
| 4,921,474 A * | 5/1990 | Suzuki et al. |
| 5,087,239 A | 2/1992 | Beastall et al. |
| 5,158,535 A | 10/1992 | Paul et al. |
| 5,267,953 A | 12/1993 | Paul et al. |
| 5,330,421 A | 7/1994 | Tarr et al. |
| 5,346,468 A | 9/1994 | Campion et al. |
| 5,350,371 A | 9/1994 | Van Iten |
| 5,395,308 A | 3/1995 | Fox et al. |
| 5,437,628 A | 8/1995 | Fox et al. |
| 5,531,674 A | 7/1996 | Frayman |
| 5,533,966 A | 7/1996 | Schoelling |
| 5,533,990 A | 7/1996 | Yeo |
| 5,614,230 A | 3/1997 | Weyenberg et al. |
| 5,683,358 A | 11/1997 | Nielsen et al. |
| 5,702,553 A | 12/1997 | Iskra et al. |
| 5,746,710 A | 5/1998 | Nielsen et al. |
| 5,788,663 A | 8/1998 | Igaue et al. |
| 5,817,047 A | 10/1998 | Osborn, III et al. |
| 5,910,520 A | 6/1999 | Dabi et al. |
| 5,958,321 A | 9/1999 | Schoelling et al. |
| 6,019,744 A | 2/2000 | Altdorf et al. |

* cited by examiner

TAMPON APPLICATOR HAVING OUTWARDLY FLARED RIM

FIELD OF THE INVENTION

The present invention relates to methods of applying an expandable sleeve to tubular workpieces to form a rim thereon and to rimmed tubular devices.

BACKGROUND OF THE INVENTION

Paperboard tampon applicators comprising a pair of telescoping cylinders are well known in the art. For example, Wiegner et al., U.S. Pat. No. 4,412,833; Beastall et al., U.S. Pat. No. 5,087,239; Hinzmann, U.S. Pat. No. 4,755,164; Huffman, U.S. Pat. No. 4,573,964; Whitehead, U.S. Pat. No. 4,508,531; Neilsen et al., U.S. Pat. No. 5,683,358; and Iskra et al., U.S. Pat. No. 5,702,553 all teach various aspects of these applicators.

Tampon applicators, whether paperboard or plastic, generally incorporate surface features at the rear or gripper end to allow the user to more or less securely hold the applicator while ejecting the tampon from the opposite end of the applicator. While molded plastic applicators can generally have pronounced gripper ends by nature of their fabrication, the gripper end configuration of paperboard applicators and applicators formed from other sheet-like materials is more limited. For example, Wiegner et al. teaches a lightly grooved grip; Beastall et al. teaches a series of more pronounced grooves forming rings in the gripper end; Hinzmann discloses both a grip area having a reduced diameter and surface indentations; and Whitehead and Huffman both teach finger grip areas having substantially reduced diameter. Each of the finger grips taught in this prior art has a limited ability to prevent finger slip during ejection of the tampon.

More recent efforts have focused on using spinning techniques to manufacture outwardly disposed rim features. For example, Neilsen et al. discloses an apparatus for forming an outwardly projecting, integral fingergrip ring on a tampon applicator. One member of the apparatus rotates with respect another to form the curl. Iskra et al. discloses a method of fabricating paperboard tampon applicators having a diameter of less than about 25 mm and having an outwardly rolled finger grip. These techniques are similar and may offer very pronounced raised features on the tubular tampon applicator elements. However, both suffer from greatly increased mechanical complexity as they require simultaneous rotation and linear movements, the surface friction generated during the process can damage the surface of the materials, and the spinning techniques require significant clamping force to resist the rotational forces applied to the workpiece. Finally, these outwardly rolled products expose their, usually, unfinished inside surface to view in the rim. Neilsen et al. also illustrates in inwardly spun rim. This process fails to provide any raised feature while is suffers from most of the disadvantages described above. The complexity inherent in and the high frictional forces generated in the spinning processes results in higher capital equipment costs and increased likelihood of relatively high levels of scrap generation. Clearly, these traits are not desirable in a manufacturing process for low-cost products such as tampon applicators.

Therefore, what is needed is a robust, simple process for applying a rim to a tubular workpiece that generates an acceptable, low-cost product without requiring added heat energy (or dissipation thereof), and without the high axial loading caused by the rotational movement.

SUMMARY OF THE INVENTION

The present invention relates to an applicator device for inserting an object into a mammalian body cavity. The applicator includes a tubular member having a rim disposed at one end thereof. The rim has a shoulder projecting outwardly from the tubular member and a return margin directed inwardly from the shoulder distal the tubular member. The invention is especially useful in manufacturing paperboard applicators, such as tampon applicators.

In addition, the invention relates to methods of making a tubular device that has a rim and is capable of inserting an object into a mammalian body cavity. In one method, a sleeve having an expandable profiling surface is inserted into an end of the tubular member, and the profiling surface is expanded to form a shoulder projecting outwardly from the tubular member adjacent the end of the tubular member. The profiling surface is collapsed inwardly away from tubular member, and a return margin is formed directed inwardly from the shoulder, distal the tubular member.

In another method, return margin of the tubular device adjacent an end is folded inwardly and superposed on an inner surface of the tubular device adjacent the folded margin. A sleeve having an expandable profiling surface is inserted into the end of the tubular device, and the profiling surface is expanded to form the rim comprising a shoulder projecting outwardly from the tubular member and the return margin. As a result, the fold between the shoulder and the return margin defines an edge of the tubular member.

As used herein in the Specification and the Claims, the term "expand" and variants thereof mean that the device modified by this term spreads or stretches out; is made greater in size, bulk, volume, or scope; or is enlarged. Thus, a segmented ring may expand by the individual segments spreading out and a ring may inflate or be deformed to acquire a greater outer circumference.

The outwardly flared rim of this invention provides a comfortable, finished edge to at least one member of an applicator, such as a tampon applicator. When formed on the plunger of such an applicator also having a barrel, the rim provides a stop to allow a user to determine when the contents of the applicator device have been fully expelled. This feature also prevents the plunger from being pushed or pulled through the barrel and being left behind in the body cavity. Finally, the rim provides an aesthetically pleasing edge to the applicator device.

DETAILED DESCRIPTION OF THE PREFERRED EMBODIMENT

While the present invention generally relates to devices having a tubular member with a rim disposed at one end thereof, the following detailed description will refer, specifically, to a tampon applicator, a particularly preferred embodiment. One of ordinary skill in the art will recognize other uses for this invention including, without limitation, applicators for other catamenial devices, such as collection cups, inflatable plugs or cups, and the like; incontinence devices; suppositories; nasal packing; and the like.

Figure 1:
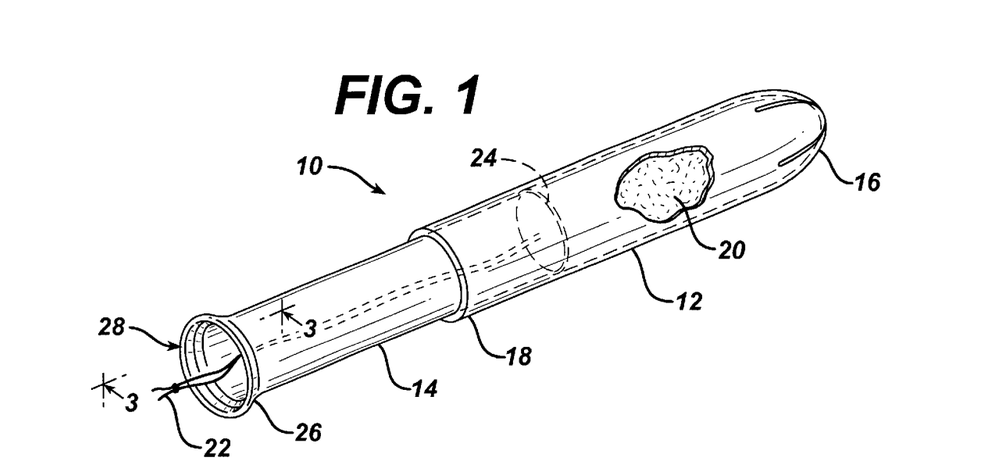
FIG. 1 is a partially broken-away, perspective view of a tampon applicator according to the present invention.
Figure 2:
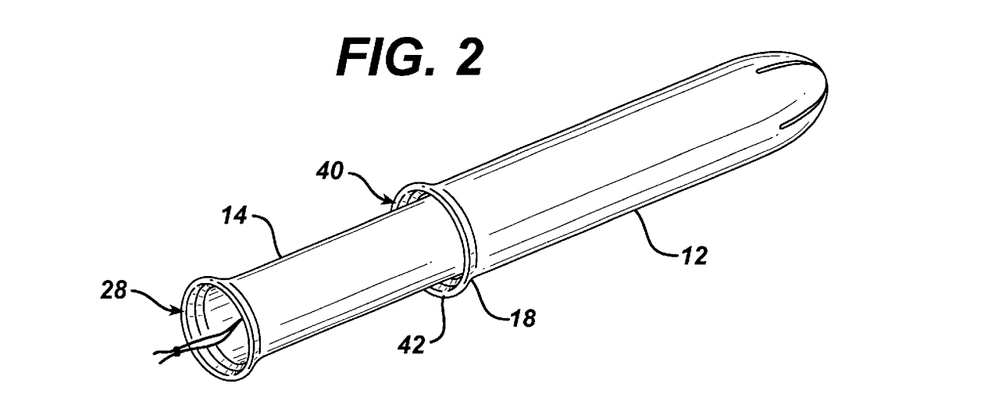
FIG. 2 is a perspective view of an alternative tampon applicator according to the present invention.

FIGS. 1 and 2 disclose a tampon applicator 10 according to the present invention formed of a barrel 12 and a plunger 14. The barrel 12 has an insertion end 16 and a gripper end 18, and it is arranged and configured to contain a tampon 20 having a withdrawal string 22.

The plunger 14 has an insertion end 24 and a gripper end 26 generally directed toward the insertion end 16 and gripper end 18 of the barrel 12, respectively. The insertion end 24 of the plunger 14 is arranged and configured to be slideably introduced into the gripper end 18 of the barrel 12.

The tampon applicator of the present invention also includes at least one rim 28 that finishes at least one edge of at least one of its components. For example, referring to FIGS. 1 and 3, the plunger 14 has a rim 28 disposed at the edge 30 associated with the gripper end 26. The rim 28 includes a shoulder 32 and a return margin 34. Either the return margin 34, itself, or a fold 36 between the shoulder 32 and the margin 34 that defines the edge 30 associated with the gripper end. The return margin 34 begins at the point or region where the material forming the rim 28 begins to return toward the interior of the tubular member, such as at point P in FIG. 3A.

In an alternative embodiment of the present invention illustrated in FIG. 2, the barrel 12 may also have a rim 40 disposed at the edge 42 associated with the gripper end 18. The rim 40 on the barrel 12 includes the features described above for the rim 28 on the plunger 14, especially with reference to FIG. 3.

Figure 3:
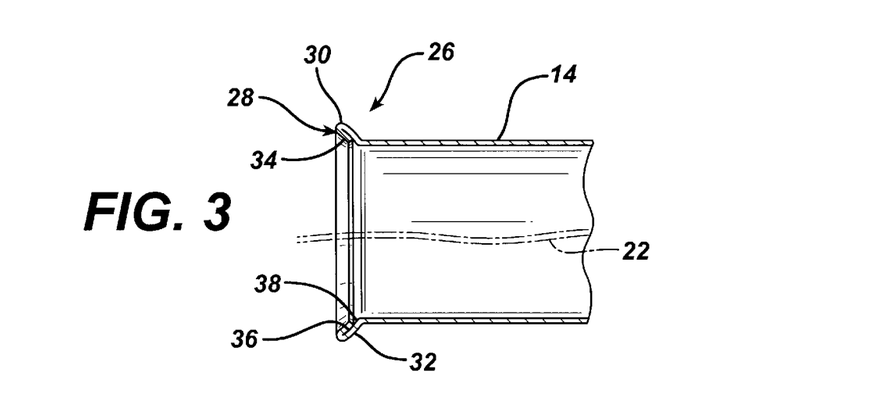
FIG. 3 is a cross-section along line 3—3 of FIG. 1.
Figure 3A:
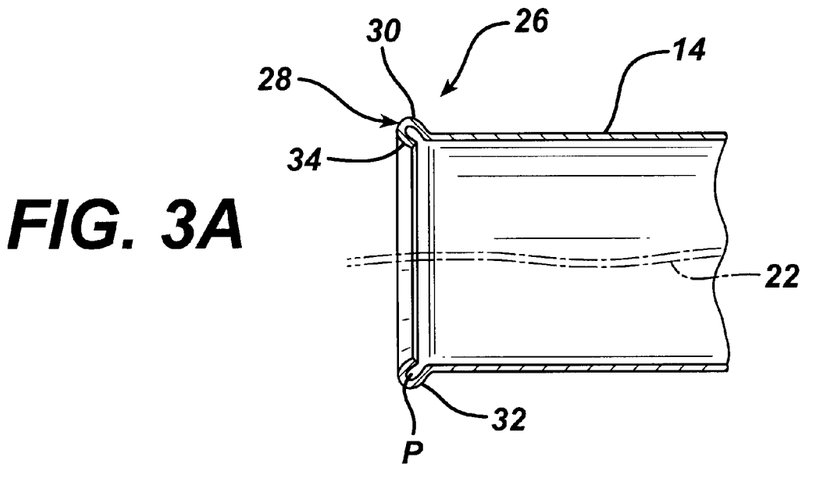
FIG. 3A is a cross-section along line 3—3 of FIG. 1 showing an alternative embodiment of the present invention.
Figure 4:
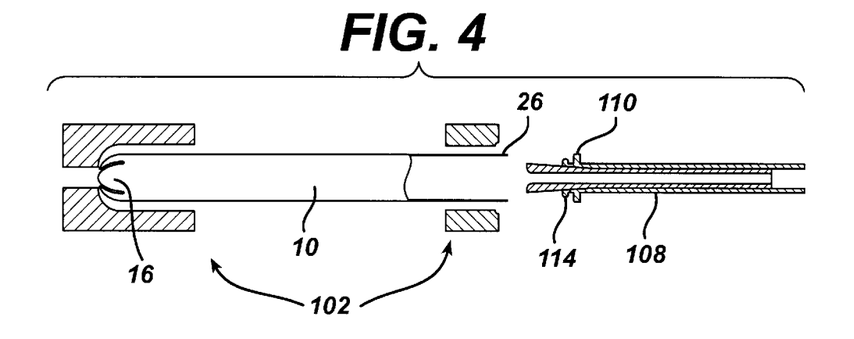
FIGS. 4–9 are cross-sections of apparatus used in various positions during their manipulation in a process according to the present invention.

In one preferred embodiment of the invention shown in FIG. 3A, the return margin 34' of the rim 28 provides a radius to the edge 30 associated with the gripper end 26 such as provided when the shoulder 32 and the return margin 34' together form an S-curve. This radiused edge 30 thereby provides a more comfortable bearing surface for a user while pressure is applied to the gripper end 26 of the plunger 14.

Alternatively as shown in FIG. 3, the return margin 34 is superposed on the inner surface 38 of the shoulder 32. Preferably, the return margin 34 is superposed on at least about half of the inner surface 38 of the shoulder 32. Again, the rim 28 provides the radius to the edge 30 due to the fold 36.

The tampon applicators 10 or other tubular devices of the present invention can have tube geometries or cross-sections that are useful to contain the object to be inserted. Often, the shape of the tampon contained suggests the shape of the barrel 12, but departures from this general rule may be made. Therefore, the barrel 12 may take on numerous cross-sectional shapes including, without limitation, circular, oval, polygonal (e.g., trapezoidal, rectangular, triangular), and the like. For example, cylindrical tampons may be contained within rectangular barrels and trapezoidal tampons (such as those disclosed in Van Iten et al., U.S. Pat. No. 5,350,371) and cup-shaped tampons (such as those disclosed in Bailey, U.S. Pat. No. 2,330,257) can be contained in a generally cylindrical barrel. In addition, the barrel 12 can substantially elongated, curved, or flexible, or it can take on other shapes that are apparent to one of ordinary skill in the art. The specific geometry, itself, is not critical to the practice of the present invention. In addition, the edge of the tubular device (both finished and unfinished) may be a standard, planar edge coincident with a plane perpendicular to the longitudinal axis of the tubular device. However, the edge may also be coincident with a plane oblique to the longitudinal axis, or it may be recessed as described in the commonly assigned, copending application of Buzot, U.S. Ser. No. 09/454,989 (herein incorporated by reference).

Preferably, the rim 28 projects outwardly from the tubular member 14 by at least about 0.1 mm, and more preferably, by at least about 1 mm, and most preferably, by at least about 3 mm. This outward projection is useful to provide a comfortable, finished edge to at least one member of an applicator, such as a tampon applicator. When formed on the plunger 14 of such an applicator 10 also having a barrel 12, the rim 28 provides a stop to allow a user to determine when the contents of the applicator device 10 have been fully expelled. This feature also prevents the plunger 14 from being pushed or pulled through the barrel 12 and being left behind in the body cavity.

While the specific tube geometry is not critical, in order for the rim 28 to provide a stop, it must create an interference with at least part of the barrel 12. This interference can be accomplished in any numbers of ways. Preferably, the interference is accomplished by configuring the rim 28 such that at least a portion of the rim 28 must project beyond an area defined by the inner dimensions of the barrel 12. For example, in a pair of cylindrical tubular members, the rim 28 of the plunger 14 should have a maximum outer diameter that is greater than the minimum inside diameter of the barrel 12. Alternatively, in a pair of tubular members in which the plunger is cylindrical and the barrel has a polygonal cross-section, the rim of the plunger should have a maximum outside diameter that is greater than the minimum inner dimension of the barrel passing through a central axis thereof. In yet another alternative, in which the plunger has a rectangular cross-section and the barrel is cylindrical, the maximum length of a side of the rim is greater than a corresponding chord of the circle defined by the inner diameter of the barrel. The term "diameter" as used in 3herein the specification and the claims means a chord passing through the center of a figure or body; the length of a straight line through the center of an object.

In reference to an applicator 10 comprising a pair of cylindrical tubular members (barrel 12 and plunger 14), it is preferred that the rim 28 on the plunger 14 has a maximum outside diameter that is greater than the minimum inner diameter of the barrel 12. More preferably, the maximum outside diameter of the rim 28 is targeted to at least equal to the outside diameter of the barrel 12. This allows for variability inherent in manufacturing processes to ensure that an interference will occur between the two members.

The applicator devices of the present invention can be made of materials generally known to those of ordinary skill in the art. The applicators may be plastic, such as injection-moldable or blow-moldable plastic, biodegradable plastic, such as those disclosed in Dabi et al., U.S. Pat. No. 5,910,520 (herein incorporated by reference), or cardboard. However, the invention is especially effective with cardboard applicators. The cardboard used in tampon applicators can be a single layer of cardboard material, or it can be a plurality of laminated layers to provide multiple benefits relating to the various layers. Useful cardboard stock for the formation of the tubular elements include, without limitation, paperboard, cardboard, cup stock, paper, and the like. The laminated cardboard material may include a surface layer or coating of plastic, wax, silicone, and the like, which may be useful to increase the comfort to the user during insertion and withdrawal. The plastic coating may include, without limitation, polyolefins such as polyethylene and polypropylene, polyesters such as polyethylene terephthalate, polycaprolactone, polyvinyl alcohol, ethylene-vinyl acetate copolymers, cellophane, and the like.

Preferred tubular element materials include laminated cardboards. Preferred laminated cardboards include plastic laminated or plastic coated cardboard materials. These plastic laminated cardboard materials may include additional layers such as adhesive layers, tie layers, and the like.

Typical dimensions for the tubular elements useful in tampon applicators include a length of about 5 to 8 cm, a diameter of about 8 to 16 mm, and thicknesses of about 0.1 to 0.6 mm. Preferably, the diameter of the inner tubular element is less than the diameter of the outer tubular element to allow for a telescopic arrangement of the inner tubular element within the outer tubular element as shown in FIG. 1. The applicators can be made by the following non-limiting processes: spiral winding as disclosed in U.S. Pat. No. 5,346,468, convolute winding as disclosed in U.S. Pat. No. 4,508,531, and forming a sheet around a mandrel and then sealing an overlapped seam as disclosed in U.S. Pat. No. 4,755,164.

Figure 5:
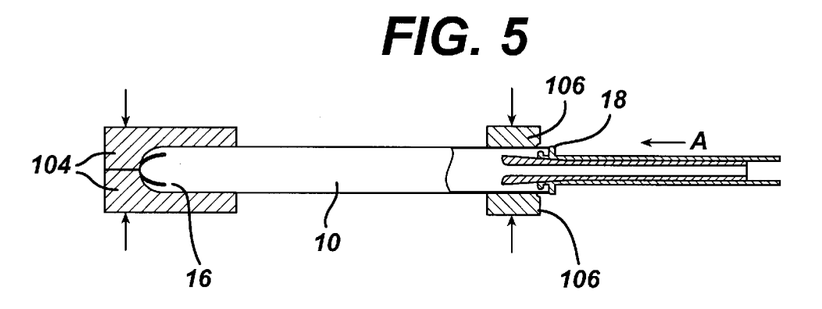

The rim 28 of the present invention may be formed by first expanding the edge 30 to form the shoulder 32 and then tucking or folding it to form the return margin 34 (the "Expand/Tuck" process shown in FIGS. 4–9). Alternatively, it may be formed by first inwardly folding the return margin 34 and then expanding it to form the shoulder 32 (the "Tuck/Expand" process shown in FIGS. 10–16). In the Expand/Tuck process, a workpiece, such as a tampon applicator 10 is placed into a holder 102. The holder 102 is capable of reciprocating movement to clamp the tampon applicator 10 to substantially immobilize it. The holder 102 preferably immobilizes both the insertion end 16 (e.g., of the barrel 12) and the gripper end 26 (e.g., of the plunger 12), and it can accomplish this by means of a single set of jaws or multiple sets of jaws. In FIG. 5, a first set of jaws 104, capable of reciprocating movement, clamps the insertion end 16 and a second set of jaws 106, capable of reciprocating movement, clamps the gripper end 26. When the tampon applicator 10 is at least partially immobilized, at least a portion of a sleeve 108 is inserted axially into the insertion end 16.

In one preferred embodiment, the tampon applicator 10 includes a barrel 12, a plunger 14, and a tampon 20, and the first set of jaws 104 clamps on the insertion end 16 of the barrel 12. Next, at least a portion of the sleeve 108 is inserted axially into the gripper end 26 of the plunger 14 as shown by arrow "A", and a flange 110 projecting radially outwardly from the sleeve 108 contacts the edge 30 of the plunger 14 to ensure that the plunger 14 is fully inserted into the barrel 12 prior to the movement of the second set of jaws 106 in to clamp and immobilize the gripper end 26 of the plunger 14.

Figure 6:
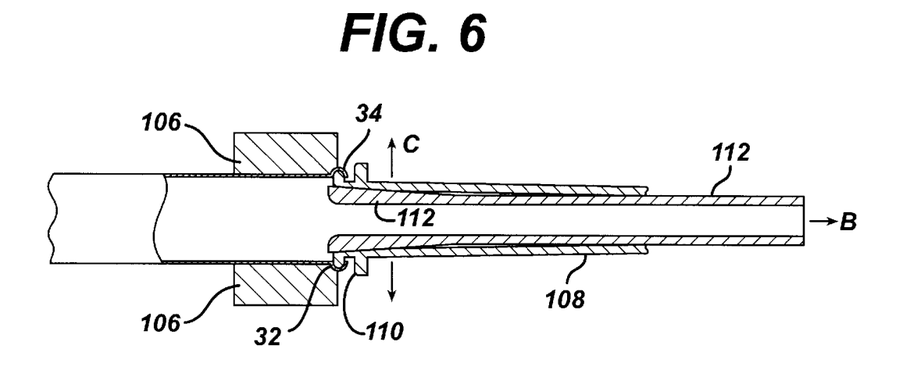

Once the sleeve 108 is inserted axially into the immobilized gripper end 26 of the plunger, a tapered ram 112 is drawn axially (as shown by arrow "B") into the sleeve 108 to cause a profiling surface 114 located on the sleeve 108 to expand radially in the direction of arrows "C" toward the inner surface 38 of the plunger 14 as shown in FIG. 6. After contact with the inner surface 38, the sleeve 108 can continue to expand radially to flare a portion of the gripper end 26 of the plunger 14 with the profiling surface 114 to form the shoulder 32. This expansion is achieved primarily, preferably completely, without any relative rotation between the profiling surface 114 and the plunger 14. As discussed above, this allows the shoulder 32 to be formed more easily than with a spinning process.

Figure 7:
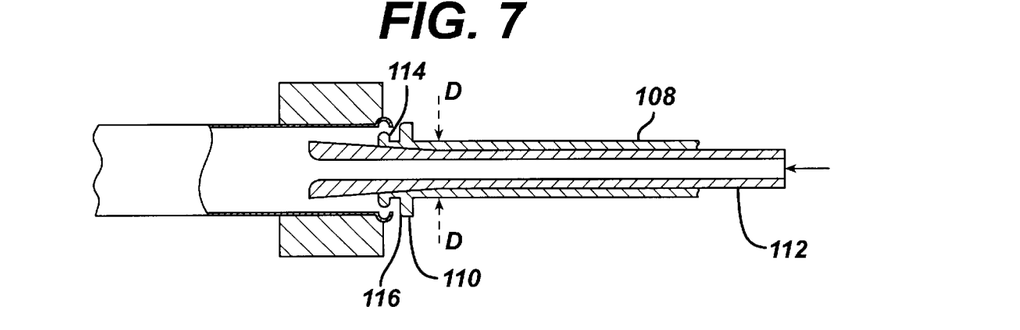
Figure 8:
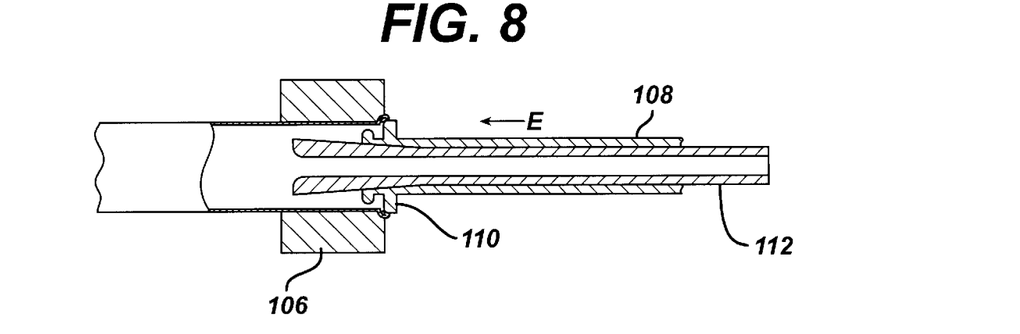
Figures 9, 9A:
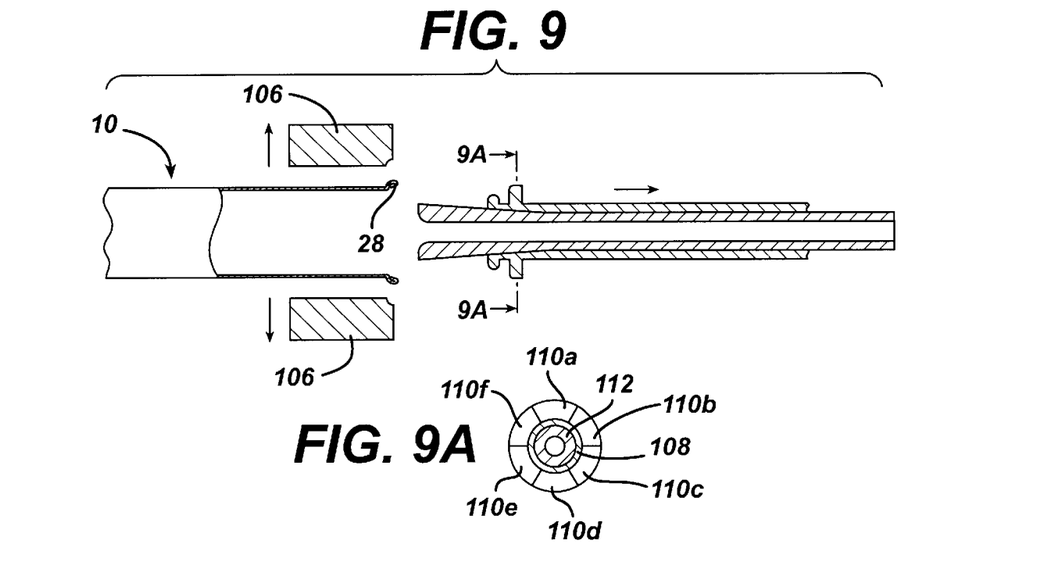
FIG. 9A is a cross-section along line 9A—9A of FIG. 9 showing a segmented expandable sleeve useful in the present invention.
Figure 10:
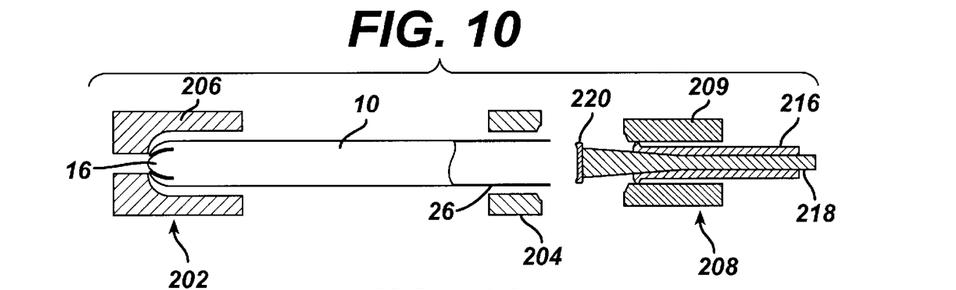
FIGS. 10–16 are cross-sections of apparatus used in various positions during their manipulation in an alternative process according to the present invention.

Referring now to FIG. 7, the tapered ram 110 is expelled axially from the sleeve 108 which retracts radially away from the shoulder 32, as indicated by arrows "D". This allows the sleeve 108 to again move axially within the gripper end 26 of the plunger 14. Indeed in an optional step, the sleeve 108 can move axially as shown by arrow "E" in FIG. 8 into the gripper end 26 to allow the flange 110, preferably an edge 116 of the flange 110, to again contact the edge 30 of the plunger 14. This contact tucks the edge 30 into the shoulder 32, preferably to superpose it on the inner surface 38, to form the rim 40. As shown in FIG. 9, the sleeve 108 can be withdrawn axially from the gripper end 26, and the jaws of the holder can retract to allow the tampon applicator 10 to be removed from the holder 102. If the return margin 34 is not required to be folded completely to a superposed position, the second set of jaws 106 may be modified to form an annular ring having, e.g., a semicircular cross-section.

The apparatus used in the Expand/Tuck process includes the holder 102 formed of first and second jaws 104, 106. These jaws 104, 106 may be portions of the same tooling, or they may be independently operable as discussed, above. The holder 102 may be considered an outer set of tooling. In addition, the apparatus includes a sleeve 108 and a tapered ram 110. The sleeve 108 may have a flange 110 and a profiling surface 114 to form the outwardly flared edge. Preferably, the flange 110 has a beveled or rounded edge 116 to provide a biased surface to initiate tucking the return margin 34 into the shoulder 32 to form the rim 40.

Figure 11:
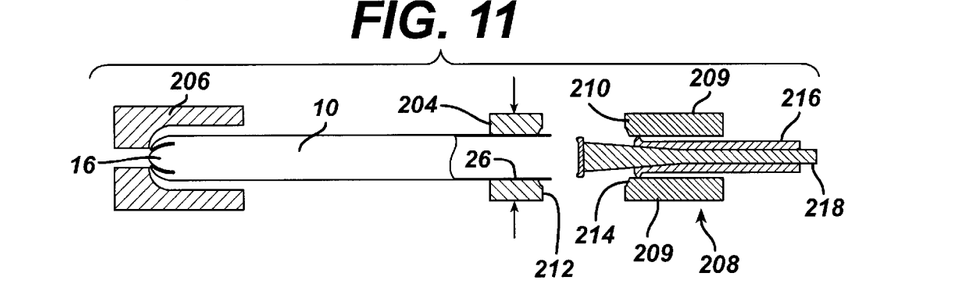
Figure 12:
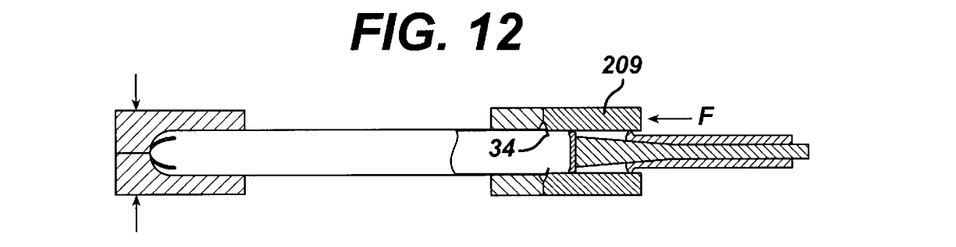

In the alternative Tuck/Expand process shown in FIGS. 10–16, a workpiece, such as a tampon applicator 10 is placed into a holder 202. The holder 202 clamps the tampon applicator 10 to substantially immobilize it. The holder 202 preferably immobilizes both the insertion end 16 and the gripper end 18, preferably by means of multiple sets of jaws. As shown in FIGS. 11 and 12, a first set of jaws 204 clamps the gripper end 18, and a second set of jaws 206 clamps the insertion end 16.

The tampon applicator 10 is immobilized in the holder 202 in a condition that exposes a predetermined length of the gripper end 18 to protrude from the first set of jaws 204 with the holder 202, tampon applicator 10, and a reciprocating set of tooling 208 axially aligned. An outer sleeve 209 of the tooling 208 moves axially in the direction of arrow "F" to bring a front face 210 of the outer sleeve 209 into contact with the rear face 212 of the first set of jaws 204. The inner diameter of the outer sleeve 209 has a diameter that is slightly less than the diameter of the holder 202, especially of the first set of jaws 204. The front face 210 has a slightly beveled edge 214 to direct the edge 30 of the gripper end 18 inwards. Thus, as the tooling 208 moves axially toward the first set of jaws 204, the beveled edge 214 contacts the edge 30 and curls the return margin 34 radially inwards.

Figure 13:
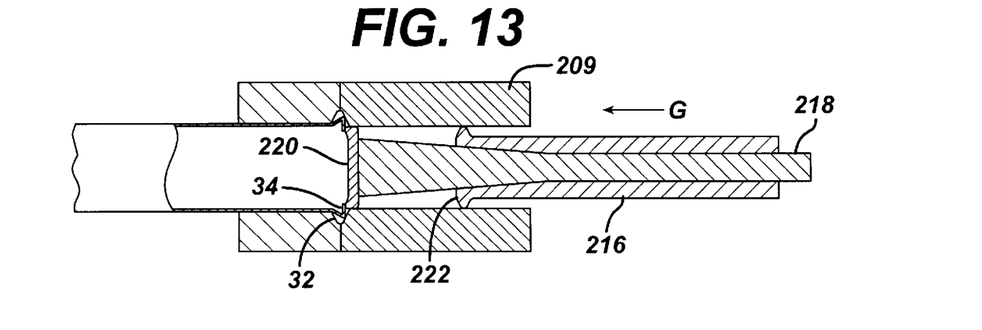
Figure 14:
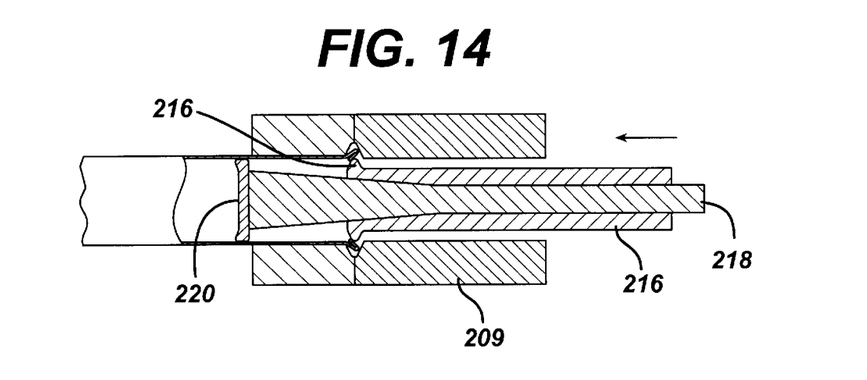
Figure 15:
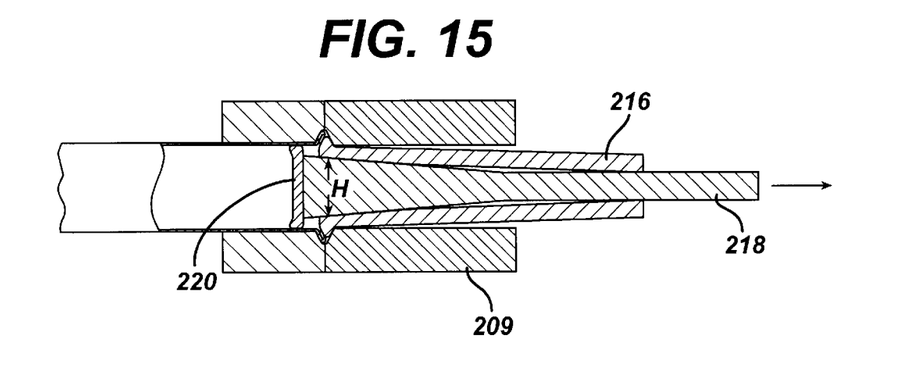
Figure 16:
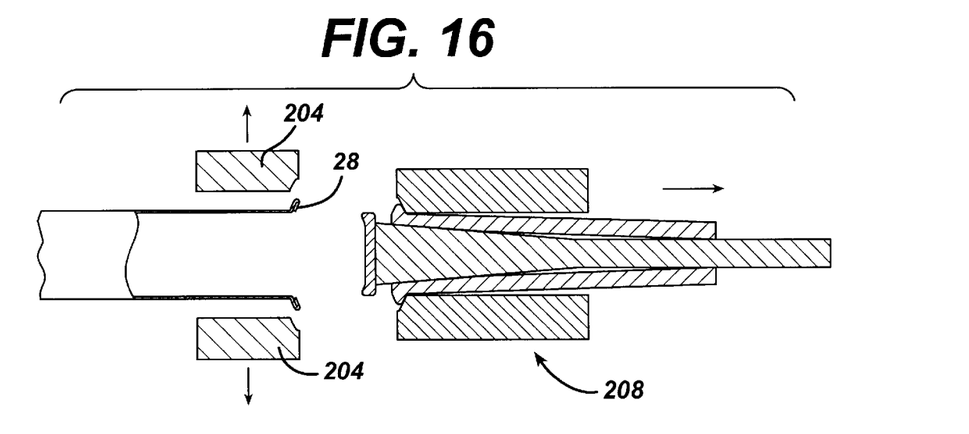

As shown in FIGS. 12 and 13, the tooling 208 has an inner, sleeve 216 and a tapered ram 218. The inner sleeve 216 and ram 218 move axially (as indicated by arrow "G") into the tampon applicator 10, and a flange 220 on the tapered ram 218 contacts the return margin 34 to tuck (or fold) it onto the inner surface 38. The ram 218 is drawn into the inner sleeve 216, and an expandable profiling surface 222 is forced radially outwards in the direction of arrows "H" to expand the rearmost portion of the gripper end 18 forming the shoulder 32 and the rim 28. Finally, the tooling 208 and the holder 202 release the tampon applicator 10, and the process is complete. Again, the expansion is achieved primarily, preferably completely, without any relative rotation between the profiling surface 222 and the tampon applicator 10.

The apparatus used in the Tuck/Expand process includes the holder 202 formed of first and second jaws 204, 206. These jaws 204, 206 may be portions of the same tooling, or they may be independently operable as discussed, above. In addition, the apparatus includes a set of tooling capable of reciprocating movement 208, comprising an outer sleeve 209, an inner sleeve 216, and a ram 218. The outer sleeve 209 preferably has a beveled edge 214 on its front face 210. The tapered ram 218 preferably has a flange 220 at its distal end, and the inner sleeve 216 preferably has a profiling surface 222 at its distal end.

The apparatus and processes have been described above with reference to specific tooling illustrated in the drawing. However, one of ordinary skill in the art will recognize that the use of such tooling is not critical and alternatives are available.

For example, expanding the sleeve is preferably achieved by the interaction of the sleeve and the ram. A ram can have a taper that is arranged and configured such that a proximal end contained within the sleeve has a smaller cross-section than a distal end projecting from the sleeve. In contrast, the taper could be arranged and configured such that a proximal end contained within the sleeve has a larger cross-section than a distal end projecting from the sleeve. Thus, a sleeve can be expanded by drawing the former tapered ram into the sleeve or it could be expanded by withdrawing the latter tapered ram out of the sleeve. Indeed, the sleeve and the expandable profiling surface could be an expanding, segmented collet as illustrated in FIG. 9A wherein the segmented, or split, profiling surface 114 forms a portion of the split sleeve 108. The flange 110 also comprises six segments 110a–110f, as illustrated.

Alternatively, the ram could be substantially cylindrical while the sleeve could be tapered in either direction. In yet another arrangement, the sleeve or features on the sleeve, such as the profiling surface and/or the flange may be extendable by means of hydraulics or air pressure.

While the preceding description has focused on an expandable, generally split, sleeve 108, the expandable profiling surface can also be achieved through technologies such as air mandrel technology and the like. In addition, the profiling surface may be segmented, as illustrated in FIG. 9A, it also may be formed of a resilient and/or elastic material, such as a deformable, continuous elastomeric o-ring that may be placed upon an expandable sleeve, even a split sleeve, or another deforming device, e.g., a linear compression device. Still other methods of extending the appropriate features on the tooling will be recognized by the ordinarily skilled artisan.

The specification above is presented to aid in the complete and non-limiting understanding of the invention disclosed herein. Since many variations and embodiments of the invention can be made without departing from its spirit and scope, the invention resides in the claims hereinafter appended.

What is claimed is:

1. An applicator device for inserting an object into a mammalian body cavity comprising a tubular member having an inner surface and a rim disposed at one end thereof, the rim comprising:

a) a shoulder projecting radially outwardly from the tubular member; and b) a return margin directed inwardly from the shoulder, toward an inner surface thereof, and distal the tubular member,
wherein the inner surface of the shoulder extends from the inner surface of the tubular insertion member.

2. The applicator device of claim 1 which further comprises a fold between the shoulder and the return margin; the return margin is superposed on the inner surface of the shoulder; and the fold between the shoulder and the return margin defines an edge of the tubular member.

3. The applicator device of claim 2 wherein the return margin is superposed on at least about half of the inner surface of the shoulder.

4. The applicator device of claim 1 wherein the tubular member comprises a thin-walled element.

5. The applicator device of claim 4 wherein the thin-walled element comprises paperboard.

6. The applicator device of claim 4 wherein the thin-walled element comprises plastic.

7. The applicator device of claim 1 wherein the tubular member has a substantially constant cross-sectional area along a length thereof.

8. The applicator device of claim 1 wherein the tubular member has a cross-sectional area that varies along a length thereof.

9. The applicator device of claim 1 wherein the shoulder and return margin together form an S-curve.

10. The applicator device of claim 1 wherein the rim has an outer diameter that is at least about 5 mm greater than a corresponding outer diameter of the tubular member.

11. The applicator device of claim 1 wherein the return margin defines a minimum inner diameter that is less than a maximum inner diameter of the shoulder.

12. An applicator device for inserting an object into a mammalian body cavity comprising a barrel and a plunger wherein a) the barrel comprises a first tubular member having an insertion end and a gripper end and is arranged and configured to slidably accept the plunger into the gripper end and to contain the object which is capable of being expelled through the insertion end;

b) the plunger comprises a second tubular member which is the tubular member of claim 1 having an insertion end capable of being slidably introduced into the gripper end of the barrel; and c) the insertion end of the plunger is disposed opposite the rimmed end of the second tubular member.

13. The applicator device of claim 12 which further comprises a fold between the shoulder and the return margin; the return margin is superposed on the inner surface of the shoulder; and the fold between the shoulder and the return margin defines an edge of the tubular member.

14. The applicator device of claim 13 wherein the return margin is superposed on at least about half of the inner surface of the shoulder.

15. The applicator device of claim 12 wherein the second tubular member has a substantially constant cross-sectional area along a length thereof.

16. The appliocator device of claim 12 wherein the shoulder and return margin together form S-curve.

17. The applicator device of claim 12 wherein the rim has an outer diameter that is greater than an inner diameter of the barrel proximate the gripper end.

18. An applicator device for inserting an object into a mammalian body cavity comprising a barrel and a plunger wherein:

a) the barrel comprises the rimmed tubular member of claim 1 having an insertion end and a gripper end comprising the rim, and the barrel is arranged and configured to slidably accept the plunger into the gripper end and to contain the object which is capable of being expelled through the insertion end; and b) the plunger comprises a tubular member having an insertion end capable of being slidably introduced into the gripper end of the barrel.

19. The applicator device of claim 18 which further comprises a fold between the shoulder and the return margin; the return margin is superposed on the inner surface of the shoulder; and the fold between the shoulder and the return margin defines an edge of the tubular member.

20. The applicator device of claim 19 wherein the return margin is superposed on at least about half of the inner surface of the shoulder.

21. The applicator device of claim 18 wherein the rimmed tubular member has a substantially constant cross-sectional area along a length thereof.

22. The applicator device of claim 18 wherein the shoulder and return margin together form an S-curve.

23. The applicator device of claim 18 wherein the rim has an outer diameter that is at least about 5 mm greater than a corresponding outer diameter of the tubular member of the barrel.

24. A tampon applicator comprising:
   a) a barrel comprising a first tubular member having an insertion end and a gripper end, wherein the barrel is arranged and configured to contain a tampon capable of being expelled through the insertion end thereof; and
   b) a plunger comprising a second tubular member having an inner surface, an insertion end arranged and configured to be slideably introduced into the gripper end of the barrel and a rim disposed at an opposite end thereof, the rim comprising:
      i) a shoulder projecting radially outwardly from the tubular member; and
      ii) a return margin directed inwardly from the shoulder, toward an inner surface thereof, distal the tubular member,
         wherein the inner surface of the shoulder extends from the inner surface of the tubular insertion member.

25. The tampon applicator of claim 24 wherein the barrel and plunger are substantially cylindrical.

26. The tampon applicator of claim 24 which further comprises a fold between the shoulder and the return margin; the return margin is superposed on the inner surface of the shoulder; and the fold between the shoulder and the return margin defines an edge of the tubular member.

27. The tampon applicator of claim 26 wherein the return margin is superposed on at least about half of the inner surface of the shoulder.

28. The tampon applicator of claim 24 wherein each tubular member has a substantially constant cross-sectional area along a length thereof.

29. The tampon applicator of claim 24 wherein the shoulder and return margin together form an S-curve.

30. The tampon applicator of claim 24 wherein the rim has an outer diameter that is greater than an inner diameter of the barrel proximate the gripper end.

31. The tampon applicator of claim 24 wherein the barrel further comprises:
   i) a shoulder projecting outwardly from the first tubular member; and
   ii) a return margin directed inwardly from the shoulder distal the first tubular member.

* * * * *